United States Patent
Amin et al.

(10) Patent No.: US 6,319,910 B1
(45) Date of Patent: Nov. 20, 2001

(54) METHOD FOR INHIBITING CYCLOOXYGENASE-2 AND TUMOR NECROSIS FACTOR ALPHA

(75) Inventors: Ashok Amin, Union, NJ (US); Steven Abramson, Rye, NY (US); Inoravadan V. Patel, Hillsborough, NJ (US)

(73) Assignee: Hospital for Joint Diseases, New York, NY (US)

( * ) Notice: Subject to any disclaimer, the term of this patent is extended or adjusted under 35 U.S.C. 154(b) by 0 days.

(21) Appl. No.: 09/213,149

(22) Filed: Dec. 17, 1998

Related U.S. Application Data (60) Provisional application No. 60/068,286, filed on Dec. 19, 1997.

(51) Int. Cl.[7] ................................................. A61K 31/65
(52) U.S. Cl. ............................................................. 514/152
(58) Field of Search ............................................... 514/152

(56) References Cited

U.S. PATENT DOCUMENTS

| | | | |
|---|---|---|---|
| 5,223,248 | 6/1993 | McNamara et al. | 424/49 |
| 5,532,227 | 7/1996 | Golub et al. | 514/152 |
| 5,789,395 | * 8/1998 | Amin et al. | 514/152 |
| 5,837,696 | * 11/1998 | Golub et al. | 514/152 |
| 5,919,775 | * 7/1999 | Amin et al. | 514/152 |

* cited by examiner

*Primary Examiner*—Kevin E. Weddington
(74) *Attorney, Agent, or Firm*—Browdy and Neimark (57) ABSTRACT

Chemically modified tetracyclines are a new class of non-steroidal anti-inflammatory drugs which inhibit cyclooxygenase-2 and tumor necrosis factor alpha. These chemically modified tetracyclines are used in a method for inhibiting COX-2, which in turn inhibits $PGE_2$, and/or inhibiting TNF$\alpha$. They are also used in a method for treating a disease or disorder associated with elevated activities of COX-2 (i.e., increased production of $PGE_2$) and/or TNF$\alpha$.

2 Claims, 6 Drawing Sheets

FIG. 4A Murine macrophages

FIG. 4B Bovine chondrocytes

METHOD FOR INHIBITING CYCLOOXYGENASE-2 AND TUMOR NECROSIS FACTOR ALPHA

CROSS-REFERENCE TO RELATED APPLICATIONS

The present application claims priority from U.S. provisional application serial No. 60/068,286, filed Dec. 19, 1997, the entire contents of which are hereby incorporated by reference.

BACKGROUND OF THE INVENTION

1. Field of the Invention

The present invention relates to methods for inhibiting cyclooxygenase-2 (COX-2) and tumor necrosis factor alpha (TNFα) activities and treating disorders and diseases associated with elevated COX-2 and TNFα activities.

2. Description of the Background Art

The two isoforms of cyclooxygenase, cyclooxygenase 1 and 2 (COX-1 and COX-2), also referred to as prostaglandin endoperoxide synthase 1 and 2, are key enzymes in the conversion of arachidonic acid to prostaglandins, thromboxanes and other eicosanoids. It is believed that COX-1 and COX-2 have different physiologic functions due to striking differences in their tissue expression and regulation. COX-1 is a constitutive enzyme that is present at all times in the body and is responsible for the production of cytoprotective prostaglandins important for homeostatic functions, such as maintaining the integrity of the gastric mucosa, mediating normal platelet function, and regulating renal blood flow. In contrast, COX-2 is a rapidly inducible form of cyclooxygenase that leads to the production of proinflammatory prostaglandins. While COX-2 expression is highly restricted under basal conditions, it is dramatically up-regulated during inflammation.

Prostaglandins are produced at elevated levels in inflamed tissues including rheumatoid synovium. The prostaglandins $PGE_1$ and $PGE_2$ contribute to synovial inflammation by increasing local blood flow and potentiating the effects of mediators, such as bradykinin and IL-1β that induce vasopermeability. $PGE_2$ has also been shown to trigger osteoclastic bone resorption, suggesting that this molecule may contribute to the pathophysiology of joint erosion in rheumatoid arthritis. The involvement of COX-2 and the elevated production of prostaglandins are associated with a variety of diseases and disorders, such as brain ischemia and cancers, as well as diseases and disorders in which elevated levels of nitric oxide is present.

Studies have indicated that nitric oxide (NO), a recently recognized multi-functional mediator produced by and acting on various cells, modulates the activity of COX-2 (Salvemini et al, 1993) and participates in inflammatory and autoimmune-mediated tissue destruction. The effect of NO on COX-2 is dose-dependent. Low levels of NO activate COX-2. In contrast, large amounts of NO produced by inducible nitric oxide synthase (iNOS) can inhibit the induction of COX-2 and suppress the formulation of COX-2 metabolites. Salvemini and co-workers recently demonstrated inhibition of inflammatory response by modulation of NO production in various animal models of inflammation. Nitric oxide formation has been found to be increased in autoimmune diseases (rheumatoid arthritis, systemic lupus erythematosus, ulcerative colitis, Crohn's disease), and several classic inflammatory symptoms (erythema, vascular leakiness) are reversed by NOS inhibitors. However, while NOS inhibitors, such as $N^G$-monomethyl-L-arginine acetate (L-NMMA), inhibit the production of NO, they also appear to have the property of augmenting $PGE_2$ production due to attenuation of NO-induced down-regulation of $PGE_2$ production. Thus, most NOS inhibitors up-regulate COX-2 and the production of $PGE_2$ in a NO-dependent manner.

Tumor necrosis factor alpha (TNFα), a pleiotropic cytokine, produces a broad scope of injurious effects which also makes it an important target for therapeutic intervention. TNFα is involved in the pathophysiology of arthritis, AIDS, cancer, autoimmune diseases (immune complex diseases), lung fibrosis, multiple sclerosis, skin DTL reactions, and bacterial and parasitic infections. The gene for human TNFα encodes a prohormone that is inserted into the cell membrane as a polypeptide with a MW of 26 kD. This membrane-bound form of TNFα is bioactive as assayed by cell cytotoxicity and has been implicated in the paracrine activities of TNFα in tissues. In response to lipopolysaccharide (LPS) and other stimuli, the 26 kD form of proTNFα is proteolytically cleaved (by a metalloprotease referred to as TNFα convertase) into a soluble 17 kD polypeptide. TNFα binds to its cognate receptors (p55 and p75) as a bioactive trimer, and signals within the cell.

Systemic exposure to soluble recombinant TNFα (in quantities that could be produced endogenously by the host during infection) causes an acute syndrome of shock and tissue injury that is virtually indistinguishable from septic shock syndrome. This effect is followed by capillary leakage syndrome, hypoxia, pulmonary edema, and multiple organ failure. Such observations highlight the importance of TNFα as an important therapeutic target for various pathophysiological conditions.

Studies in animal models of arthritis and human rheumatoid arthritis indicate that TNFα may be a pivotal cytokine involved in these disease processes. Injection of anti-TNFα antibodies and/or soluble TNFα receptor has proven to be highly effective in reducing clinical signs and symptoms in controlled studies. Extension of these studies in phase II and III clinical trials (in rheumatoid arthritis) has yielded very encouraging results, again indicating that neutralizing the effects of TNFα may have profound effects on disease progression in various inflammatory diseases, including arthritis.

The matrix metalloproteases (MMPs) have long been recognized to play an important role in cartilage degradation in both rheumatoid arthritis (RA) and osteoarthritis (OA). The synovium and cartilage are the most important sources of degradative enzymes that contribute to the pathophysiology of OA and RA. These enzymes include metalloproteases, serine proteases, proteoglycanases and thiol proteases. The two main families of MMPs believed to be responsible for cartilage degradation are collagenases and proteoglycanases.

Early studies by three independent groups have demonstrated that broad-spectrum inhibitors of matrix metalloproteases can specifically inhibit the release of membrane proTNFα (but not IL-1β or IL-6) from various cell surfaces, including rheumatoid arthritis synovial cell cultures. This inhibitor of proTNFα processing could protect mice against a lethal dose of administered endotoxin. The "TNFα convertase" activity was isolated using these inhibitors as ligands by affinity purification which resulted in identification of an 80 kD protein with the capacity to cleave the Gln-Ala-↓-Val-Arg (SEQ ID NO:1) sequence of proTNFα.

Doxycycline and minocycline are members of the tetracycline family of broad-spectrum antibiotics. During recent years, it has been established that tetracyclines, which are rapidly absorbed and have a prolonged half-life, exert biological effects independent of their antimicrobial activity (Golub et al, 1991; Golub et al, 1992; Uitto et al, 1994). Such effects include inhibition of matrix metalloproteases, including collagenase (MMP-1), gelatinase (MMP-2) and stromelysin (MMP-3) activity, and prevention of pathogenic tissue destruction (Golub et al, 1991). In inflammatory arthritides such as rheumatoid arthritis, these matrix metalloproteases have been identified in homogenates and cultures of rheumatoid synovium, detected in inflammatory synovial fluids and localized immunologically and by in situ hybridization in proliferative pannus and synovium (Brinckerhoff, 1991). These metalloproteases are known to be up-regulated in OA-affected joints (Greenwald, 1994; Mohtai et al, 1993). Interestingly, Yu et al (1992) have also shown that prophylactic administration of doxycycline markedly reduced the severity of OA in dog models. To assess the safety and efficacy of minocycline (a semisynthetic tetracycline) in the treatment of arthritis, a double-blind, randomized, multicenter trial indicated that the drug was safe and effective for patients with mild and moderate arthritis (Tilley et al, 1995). Furthermore, recent studies have also suggested that tetracyclines and inhibitors of metalloproteases inhibit tumor progression (DeClerck et al, 1994), bone resorption (Rifkin et al, 1994) and angiogenesis (Maragoudakis et al, 1994), and may have anti-inflammatory properties (Ramamurthy et al, 1994).

The laboratory of the present inventors recently observed that tetracycline and chemically modified tetracyclines inhibit nitric oxide production in macrophages and OA-affected cartilage where NOS expression is inhibited at the level of post transcriptional modification of NOS (Amin et al, 1995b, 1997b). The laboratory of the present inventors have also recently observed that human arthritis-affected cartilage in ex vivo conditions (in the absence or presence of cytokines+endotoxins) releases substantial amount of NO and $PGE_2$, and the specific inhibition of NO production augments $PGE_2$ production in a NO-dependent fashion (Amin et al, 1997a).

Tetracyclines have also been found to be effective for treating collagenase activity in periodontal disease and diabetes (U.S. Pat. No. 4,666,897 and No. 4,704,383), for inhibiting excessive phospholipase $A_2$-activity (U.S. Pat. No. 5,523,297), and for inhibiting elastase activity (U.S. Pat. No. 5,773,430)

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention relates to the discovery that chemically-modified tetracyclines (CMTs) with negligible anti-microbial activity are a new class of non-steroidal anti-inflammatory drugs (NSAIDs) which inhibit cyclooxygenase-2 (COX-2) and tumor necrosis factor alpha (TNFα) activities.

Accordingly, it is an object of the invention to provide a method for inhibiting COX-2 and/or TNFα in a biological system.

Another object of the present invention is to provide a method for treating a disease or disorder associated with elevated TNFα and/or levels of products of COX-2 activity in subjects in need thereof.

DETAILED DESCRIPTION OF THE INVENTION

The present invention is based on the discovery that chemically modified tetracyclines inhibit TNFα and COX-2. These chemically modified tetracyclines contain changes to the basic structure of the tetracycline ring system or replacement of substituents at positions 1–4 or 10–12 of the ring system. Such chemically modified tetracyclines, which have negligible, or altogether lack, antimicrobial activity, are used in a method for inhibiting COX-2 and TNFα according to the present invention.

The laboratory of the present inventors evaluated the action of chemically modified tetracyclines on the spontaneous release of $PGE_2$ from OA-affected human cartilage in ex vivo conditions and on COX-2 in LPS-stimulated murine macrophages and found that the chemically modified tetracycline, 6-demethyl-6-deoxy-4-dedimethylaminotetracycline (CMT-3), which was previously shown to inhibit NOS activity, also inhibits COX-2 activity independent of intracellular NO concentrations. Furthermore, addition of a chemically modified tetracycline, 6-α-deoxy-5-hydroxy-4-dedimethylamino tetracycline (CMT-8), to human OA-affected cartilage spontaneously releasing NO and $PGE_2$ inhibited both NO and $PGE_2$ production. Without being bound by theory, it is believed that this inhibition of COX-2 may be due to inhibition of glycosylation of COX-2, a mechanism which affects COX-2 expression but would be distinct from that observed with iNOS where chemically modified tetracyclines block iNOS mRNA expression (Amin et al, 1997b). However, it is also possible that the inhibition of COX-2 is due to truncation of COX-2 or a combination of both of the above possibilities since there is evidence (Example 4) that, in the presence of chemically modified tetracyclines, there is a decrease in the molecular weight of COX-2.

Like the NOS inhibitor NMMA, commercial tetracyclines with antimicrobial activity, such as doxycyclines and minocyclines, also inhibit NO production. Chemically modified tetracycline, CMT-3 and CMT-8, with no antimicrobial activity, were found to share with tetracyclines the property of inhibiting NO production by inhibiting iNOS mRNA expression. However, whereas doxycycline and minocycline, like most other NOS inhibitors, up-regulate COX-2 expression and $PGE_2$ production in a NO-dependent manner, it was unexpectedly discovered that CMT-3 and CMT-8 inhibits COX-2 expression and $PGE_2$ production as well. This divergent property of chemically modified tetracyclines was also observed in other cells types, such as bovine chondrocytes and murine macrophages.

Non-steroidal anti-inflammatory drugs (NSAIDs) are a structurally diverse class of drugs, which include aspirin and sodium salicylate, share the important property of inhibiting prostaglandin biosynthesis. However, these actions are by no means sufficient to explain all the effects of NSAIDs. Some members of NSAIDs appear to have anticarcinogenic properties as reported in epidemiological studies with humans and in experimental carcinogenesis studies with animals. While the mechanism of the anticarcinogenic effect of NSAIDs is not known, the inhibition of COX-2 and the subsequent reduction in prostaglandin levels in tissue was suggested to be involved.

As COX-2 inhibitors, chemically modified tetracyclines are considered by the present inventors to be a new class of NSAIDs which appear to block NOS activity by a mechanism(s) quite different from known COX-2 inhibitors, such as conventional NSAIDs. The effects of conventional NSAIDs generally occurs at high dosage levels and are sometimes associated with gastric and renal toxicity. CMTs avoid these adverse side effects.

An important feature of chemically modified tetracyclines which inhibit NOS and COX-2 is their inability to completely inhibit NO or $PGE_2$ production. Rather, these chemically modified tetracyclines inhibit by dampening the over production of NO and $PGE_2$. This is a valuable property because both NO and $PGE_2$ are pleiotropic molecules with respect to cellular functions, and complete inhibition of NOS and COX-2 may be detrimental, e.g., low levels of $PGE_2$ and NO may be important for homeostasis and normal cellular functions.

Besides the ability to inhibit COX-2, chemically modified tetracyclines, such as 4-dedimethylaminotetracycline (CMT-1), CMT-3 and CMT-8, also have the important property of inhibiting TNFα. Human HEK 293 cells permanently transfected with a cDNA for proTNFα spontaneously release TNFα into the culture medium. This release of TNFα was found to be blocked by the addition of low levels of chemically modified tetracyclines, similar to what was observed with cycloheximide. Current technologies for blocking TNF activity are directed to blocking receptors for TNF or to neutralizing TNF activity with antibodies. In contrast, chemically modified tetracyclines are believed to block the release of TNF from the cell surface or to block the biosynthesis of proTNF within the cell.

As a new class of NSAIDs, chemically modified tetracyclines are preferably those which lack the dimethylamino group at position 4 of the ring structure. Preferred chemically modified tetracyclines include 4-dedimethylaminotetracycline (CMT-1), 6-demethyl-6-deoxy-4-dedimethylaminotetracycline (CMT-3), and 6-α-deoxy-5-hydroxy-4-dedimethylaminotetracycline (CMT-8). CMTs are described in U.S. Pat. No. 4,704,383, No. 4,935,411, No. 4,935,412, No. 5,459,153, No. 5,523,297, No. 5,773,430 and No. 5,789,395.

According to the present invention, an effective amount of a chemically modified tetracycline is used in a method for inhibiting COX-2 and/or TNFα and in a method for treating a disease or disorder associated with elevated levels of TNFα and/or COX-2, which lead to, for example, increased production of $PGE_2$. An effective amount of a chemically modified tetracycline is an amount that is effective to inhibit or dampen COX-2 and/or TNFα expression or activity and which is sufficient for reducing the level of TNFα and/or COX-2 products, e.g., $PGE_2$, in the biological system or subject treated.

U.S. patent application Ser. No. 08/697,815, filed Aug. 30, 1996, herein incorporated entirely by reference, discloses inhibition of NOS using chemically modified tetracyclines. While NOS activity may also be inhibited, it is intended that the method according to the present invention be directed to the inhibition of COX-2 and/or TNFα in diseases and disorders associated with enhanced levels thereof. Preferably, the present method treats diseases and disorders in which TNFα and/or the products of COX-2 are elevated but not the level of NO.

Non-limiting examples of diseases and disorders associated with enhanced COX-2 activity and elevated levels of COX-2 products treatable by the method of the present invention include brain ischemia, inflammatory bowel disease, neurodegenerative disorders, and cancers such as adenomatous polyposis, colon cancer, breast cancer and prostate cancer, etc. Non-limiting examples of diseases and disorders associated with elevated levels of TNFα treatable by the method of the present invention include multiple sclerosis, septic shock, periodontal disease, graft-vs.-host disease, cerebral malaria and cachexia associated with cancer or HIV infection. Accordingly, the method of the present invention can be used to prevent, inhibit, or alleviate such COX-2 and/or TNFα-related conditions.

As used herein, the term "prevention" of a condition, in a subject in need thereof, involves administration of the chemically modified tetracycline as the active principal prior to the clinical onset of the disease or disorder. The terms "treatment" or "treating" involves administration of the active principal preferably in a composition after the clinical onset of the disease. For example, successful administration of chemically modified tetracyclines, after development of the symptoms comprises "treatment" of the disease or disorder. While the invention is particularly useful in the treatment of humans, it is intended for veterinary uses as well.

The active principal used in the present invention may be administered by any means that achieves its intended purpose, e.g., to treat diseases and disorders associated with elevated $PGE_2$ and TNFα levels.

For example, administration may be by various parenteral routes, such as subcutaneous, intravenous, intradermal, intramuscular, intraperitoneal, intranasal, transdermal, or buccal routes. Alternatively, or concurrently, administration may be by the oral route. Parenteral administration can be by bolus injection or by gradual perfusion over time. Perioral administration can be by tablet, capsule (including controlled release capsule), or a suspension, syrup or other liquid formulation.

A typical regimen for preventing, suppressing, or treating a condition associated with elevated levels of $PGE_2$ and/or TNFα, comprises administration of a therapeutically effective amount of the chemically modified tetracycline administered over a period of time, up to and including between one week and about twelve months.

It is understood that the dosage administered will be dependent upon the age, sex, health, and weight of the recipient, kind of concurrent treatment, if any, frequency of treatment, and the nature of the effect desired. The ranges of effective doses provided below are not intended to be limiting and represent preferred dose ranges. However, the most preferred dosage will be tailored to the individual subject, as is understood and determinable by one of skill in the art. See, e.g., Avery's Drug Treatment: Principles and Practice of Clinical Pharmacology and Therapeutics, 3rd edition, ADIS Press, LTD., Williams and Wilkins (Baltimore, Md., 1987); Ebadi, Pharmacology, Little, Brown and Co. (Boston, 1985), which references are entirely incorporated herein by reference.

The total dose required for each treatment may be administered by multiple doses or in a single dose. The chemically modified tetracycline may be administered alone or in conjunction with other therapeutics directed to the condition, or directed to other symptoms of the condition.

Preferably, a CMT is administered in a pharmaceutically acceptable carrier or excipient. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in Remington's Pharmaceutical Sciences by F. W. Martin.

Therapeutically effective amounts of chemically modified tetracyclines are from about 0.1 to about 100 mg/kg body weight/day and any range therein, preferably from about 1 to about 18 mg/kg body weight/day.

Preparations for parenteral administration include sterile aqueous or non-aqueous solutions, suspensions, and emulsions, which may contain auxiliary agents or excipients which are known in the art. Pharmaceutical compositions, such as tablets and capsules, can also be prepared according to routine methods. Compositions which can be administered rectally include suppositories.

Pharmaceutical compositions comprising the chemically modified tetracyclines for use according to the method of the present invention include all compositions wherein a chemically modified tetracycline is contained in an amount effective to achieve its intended purpose. In addition, the pharmaceutical compositions may contain suitable pharmaceutically acceptable carriers comprising excipients and auxiliaries which facilitate processing of the active compounds into preparations which can be used pharmaceutically. The pharmaceutical compositions generally contain from about 0.01 to 99 percent, preferably from about 20 to 75 percent of the active principal (chemically modified tetracyclines) together with the excipient.

Suitable formulations for parenteral administration include aqueous solutions of the active compounds in water-soluble form, for example, water-soluble salts. In addition, suspension of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

Having now generally described the invention, the same will be more readily understood through reference to the following examples which are provided by way of illustration and is not intended to be limiting of the present invention.

EXAMPLE 1

Figure 1:
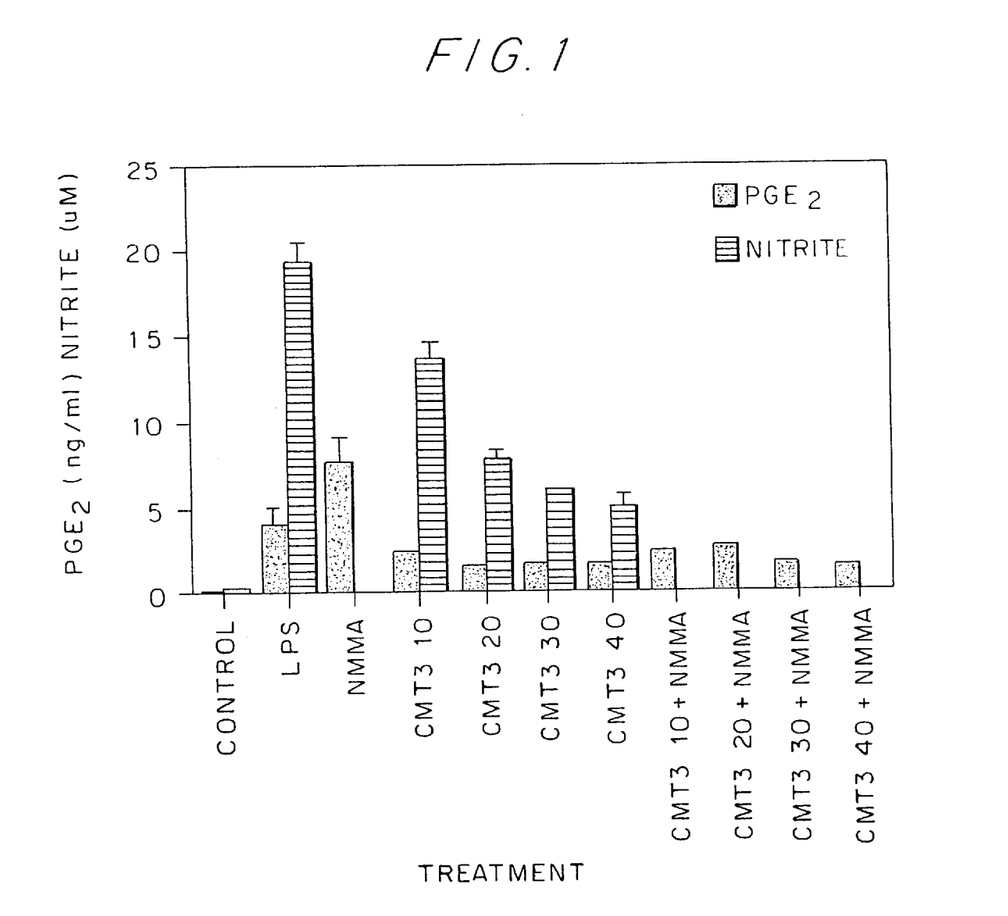
FIG. 1 shows the effect of CMT-3 and NMMA on nitrate and $PGE_2$ production in LPS-stimulated RAW 264.7 cells.

Effect of CMT-3 and NMMA on Nitrite and $PGE_2$ Production in LPS-Stimulated RAW 264.7 Cells Murine macrophages (RAW 263.7 cells) which were grown in Dulbecco's modified eagle medium (DMEM) containing 10% fetal bovine serum, 2 mM glutamine, 50 U/ml penicillin and 50 µg/ml streptomycin, were stimulated with 100 ng/ml LPS to induce both NOS and COX-2 at 16 hr. Addition of N-monomethyl arginine (L-NMMA), a competitive inhibitor of NOS, at 0 hrs blocks NO production but augments $PGE_2$ production as examined at 16 hours post stimulation as shown in FIG. 1. Addition of CMT-3 blocks both NO and $PGE_2$ production. Addition of both (CMT-3+ L-NMMA) blocks the augmentation of $PGE_2$ induced by L-NMMA, indicating that CMT-3 blocks L-NMMA induced $PGE_2$ production (FIG. 1). CMT-3 and L-NMMA share the property of inhibiting NO production, but are distinct in their property of modulating $PGE_2$ production. The data presented in FIG. 1 represents mean±SD as examined by T test were n=3.

The effects of CMTs 1, 2, 3, 5 and 8 on PGE2 and NO accumulation in RAW 264.7 cells were further evaluated as described above for CMT-3. The results are shown in Table 1.

TABLE 1

Effect of CMTs on $PGE_2$ Accumulation in Murine Macrophages Stimulated with LPS

| | EXPERIMENT I | | | | EXPERIMENT II | | | |
|---|---|---|---|---|---|---|---|---|
| | $PGE_2$/ng/ml | % Inhibition or (Increase) | Nitrite (µM) | % Inhibition | $PGE_2$/ng/ml | % Inhibition or (Increase) | Nitrite (µM) | % Inhibition |
| Control | ND | — | — | — | ND | — | — | — |
| LPS (100 ng/ml) | 25.6 ± 4.8 | — | 50.5 ± 2.3 | — | 19.5 ± 5.0 | — | 22.3 ± 0.9 | — |
| + CMT-1 (10 µg/ml) | 31.5 ± 2.5$^a$ | — | 50.8 ± 1.8$^a$ | — | 30.2 ± 8.0$^b$ | — | 20.3 ± 0.4$^b$ | — |
| + CMT-2 (10 µg/ml) | 26.8 ± 8.8$^a$ | — | ND | — | 22.9 ± 5.0$^a$ | — | 23.3 ± 3.5$^a$ | — |
| + CMT-3 (10 µg/ml) | 8.7 ± 2.4$^c$ | 66 | 24.7 ± 1.9$^c$ | 48 | 6.5 ± 0.5$^c$ | 67 | 11.7 ± 0.5$^c$ | 46 |
| + CMT-5 (10 µg/ml) | 31.5 ± 4.5$^b$ | — | ND | — | 20.2 ± 4.0$^b$ | — | 23.1 ± 3.0$^b$ | — |
| + CMT-8 (10 µg/ml) | 27.2 ± 3.4$^a$ | — | 36.0 ± 2.0$^c$ | 28 | 24.3 ± 4.5$^a$ | — | ND | — |

TABLE 1-continued

Effect of CMTs on PGE$_2$ Accumulation in Murine Macrophages Stimulated with LPS

| | EXPERIMENT I | | | | EXPERIMENT II | | | |
| --- | --- | --- | --- | --- | --- | --- | --- | --- |
| | PGE$_2$/ng/ml | % Inhibition or (Increase) | Nitrite ($\mu$M) | % Inhibition | PGE$_2$/ng/ml | % Inhibition or (Increase) | Nitrite ($\mu$M) | % Inhibition |
| + Minocycline (40 $\mu$g/ml) | 43.7 ± 8.6$^c$ | (172) | 4.8 ± 0.4$^e$ | 90 | 49.1 ± 10.0$^c$ | (257) | 12.9 ± 2.0$^d$ | 41 |
| + Hydrocortisone (10 $\mu$g/ml) | 12.3 ± 2.6 | 52 | 34.3 ± 1.3$^e$ | 32 | 9.5 ± 0.5$^e$ | 50 | 12.9 ± 0.2$^d$ | 40 |

Murine macrophages (RAW 264.7 cells) were stimulated with LPS (100 ng/ml) in the presence of 40 $\mu$g/ml minocycline, 10 $\mu$M of hydrocortisone and 10 $\mu$g/ml of CMTs in triplicate for 16 hours. Data are expressed as PGE$_2$ or nitrite accumulated in triplicate determinants (n − 3). Statistics (between LPS-stimulated cells and experimental) were derived using unpaired Student's t-test. P = $^a \leq 0.4$; $^b \leq 0.1$; $^c \leq 0.01$; $^d \leq 0.01$; $^e \leq 0.00001$. ND = Not Done.

EXAMPLE 2

Figure 2:
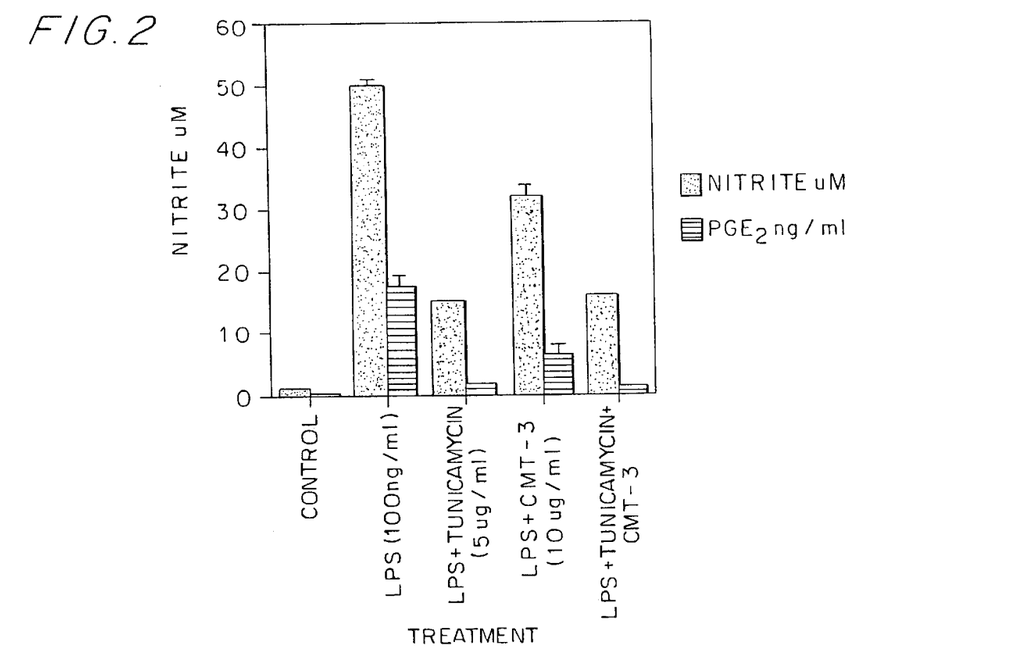
FIG. 2 shows the effect of CMT-3 and tumicamycin on nitrite and $PGE_2$ production in RAW 264.7 cells.

Effect of CMT-3 and Tunicamycin on Nitric Oxide and PGE$_2$ Production in RAW 264.7 Cells RAW 263.7 cells were grown as previously described (Amin et al, 1995b). Murine macrophages stimulated with 100 ng/ml LPS were incubated with CMT-3 or tunicamycin (a glycosylation inhibitor). As shown in FIG. 2, tunicamycin and CMT-3 inhibit both NOS/COX-2 expression and NO/PGE$_2$ production. Nitrite and PGE$_2$ were estimated as previously described (Amin et al, 1995b). It is quite possible that CMT-3 may inhibit COX-2 and PGE$_2$ production by post translational modification of COX-2 which may be similar to tunicamycin inhibition. The data represents the mean±SD evaluated by T test (n=3).

EXAMPLE 3

Figure 3:
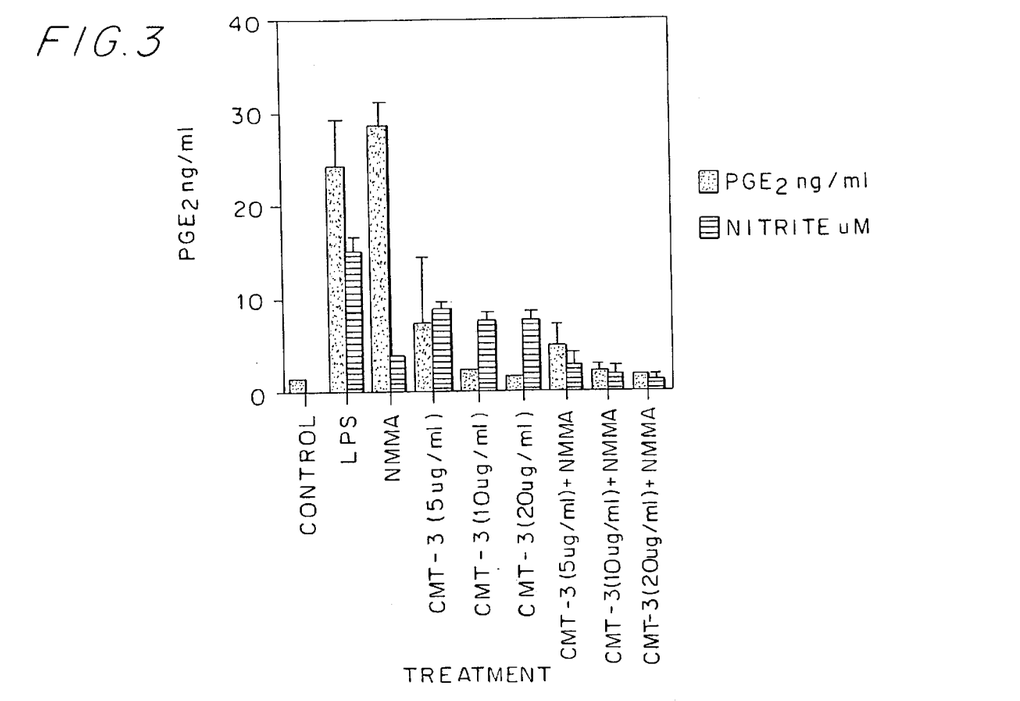
FIG. 3 shows the effect of CMT-3 on nitrite and $PGE_2$ production in liposaccharide stimulated bovine chondrocytes.
Figure 9:
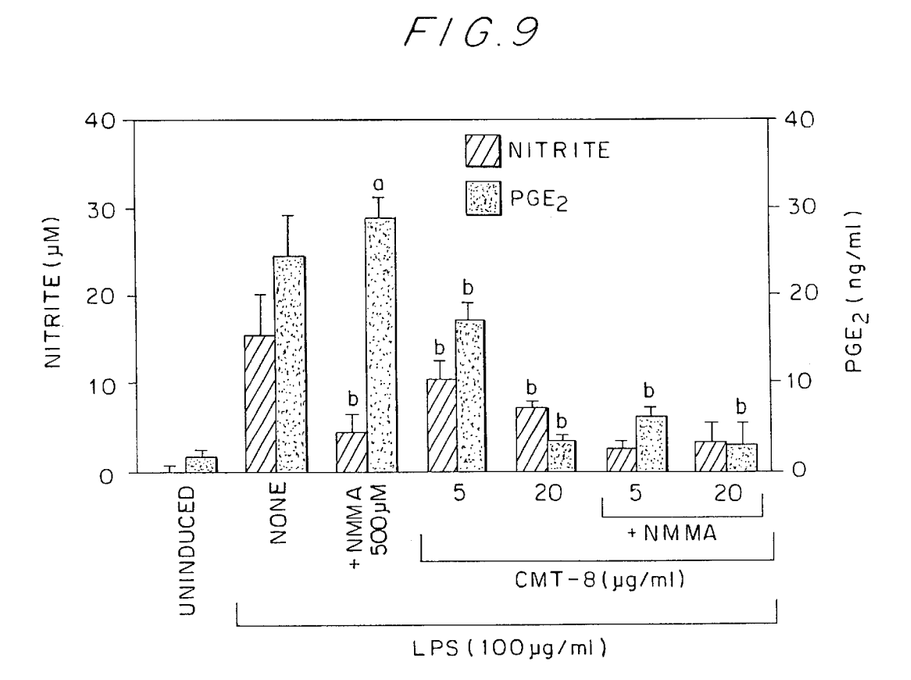
FIG. 9 shows the effect of CMT-8 on nitrite and $PGE_2$ production in lipopolysaccharide stimulated bovine chondrocytes.

Effect of CMT-3 on Nitrite and PGE$_2$ Production in LPS Stimulated Bovine Chrondrocytes Bovine chrondrocytes were isolated by the standard method of Aydelotte et al (1988) with minor modifications. Briefly, normal bovine cartilage was washed in RPMI-1640 and cut into small pieces and digested with enzymes. Cartilage pieces were incubated with trypsin (0.25%) in RPMI-1640 (Gibco BRL, Gaithersburg, Md.) for 30 minutes at 37° C. before they were washed and reincubated in hyaluronidase (0.2%) and collagenase (0.2%), dissolved in RPMI-1640 containing 5% fetal bovine serum (FBS) for 16 hr at 37° C. with continuous agitation (100 rpm). The cells were passed through 75 $\mu$M nylon mesh and washed twice with PBS to remove cell debris. The released cells were suspended in RPMI 1640+10% FBS+antibiotics and plated. After 48 hours the medium was changed and the cells were incubated with CMT-3 or N-monomethyl arginine (NMMA) for 2 hours before stimulating them with 100 $\mu$g/ml LPS. DMSO was used as a carrier for the modulators and the DMSO concentration was maintained (<0.01% v/v) in the cultures. Equivalent amounts of DMSO was also added to the control cultures. The levels of COX-2 dependent PGE$_2$ release was assayed after 72 hrs by radioimmunoassay. As observed with the murine macrophage cells, L-NMMA augments PGE$_2$ production and inhibits NO production. CMT-3 and CMT-8 both inhibit NO and PGE$_2$ production (FIGS. 3 and 9). The results in FIGS. 3 and 9 also demonstrate that CMT-3 and CMT-8 inhibits the L-NMMA induced PGE$_2$ up-regulation in bovine chondrocytes, an effect that was also observed in murine macrophages. The data represents mean±SD which was evaluated by T test where n=3.

EXAMPLE 4

Modification of COX-2 by CMT-3

Figure 4A:
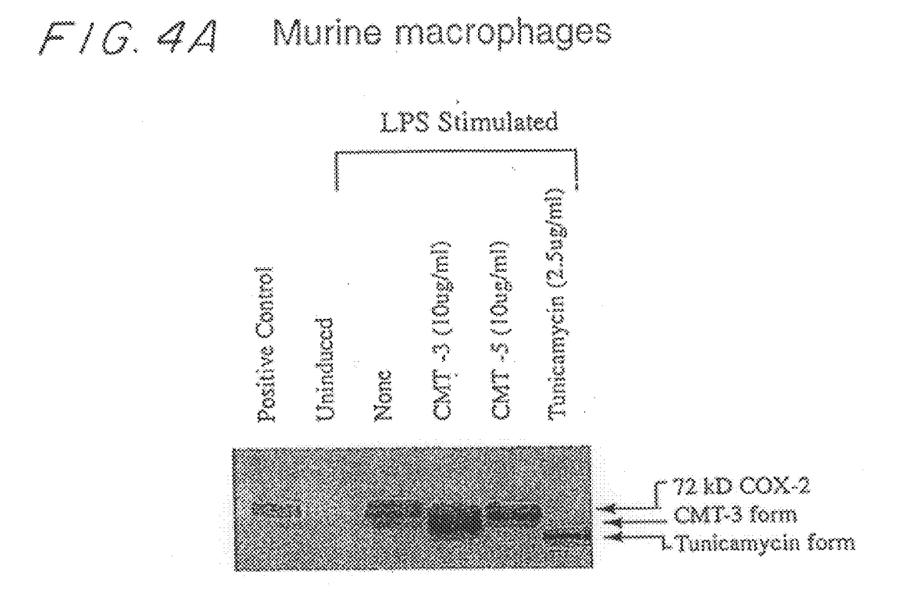
FIGS. 4A and 4B shows Western blots of cell extracts of murine macrophage (FIG. 4A) and bovine chondrocytes (FIG. 4B) to anti-COX-2 antibody.

Murine macrophage cells were cultivated as previously described (Amin et al, 1995b). Raw 267.3 cells were stimulated with 100 ng/ml of LPS in the presence of CMT-3, CMT-5 and glycosylation inhibitor, tunicamycin. The cells were grown for 16 hr and harvested. The cell free extracts were prepared as previously described (Amin et al, 1995b). In FIG. 4A, 50 $\mu$g of protein was loaded in each well and run on SDS-PAGE gels and blotted onto Western blots using a specific anti COX-2 antibody as previously described (Amin et al, 1997a). The positive control is a standard COX-2. In the CMT-3 treated cells, there is a decrease in the size of COX-2. The size is approximately 2000 D smaller (CMT-3 form) than the native COX-2 shown as a standard. CMT-5 has no significant effect whereas the tunicamycin treated cells was much smaller than the native form (tunicamycin form). These experiments indicate that CMT-3 induces modification of the COX-2 protein. The SDS PAGE analysis and Western blotting of COX-2 was carried out as described above.

Figure 4B:
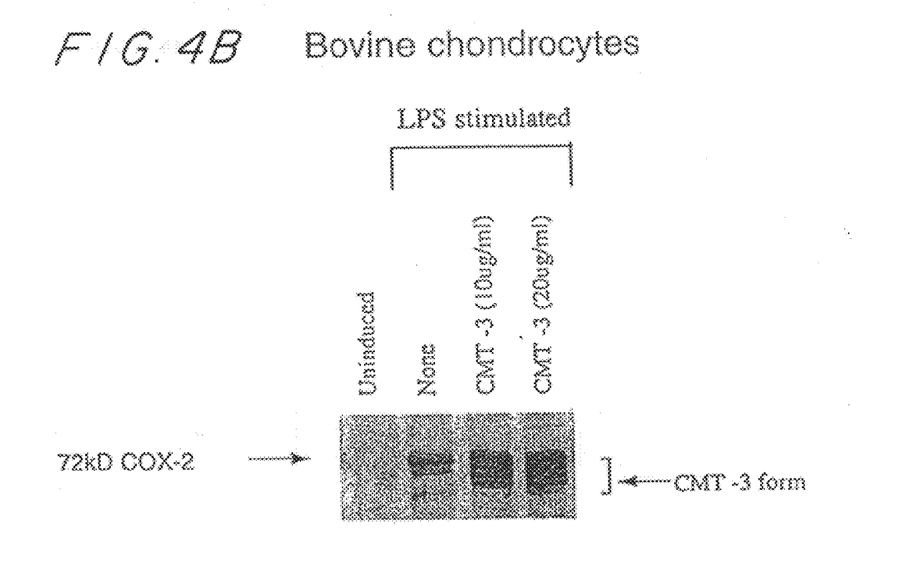

Bovine chondrocytes were isolated as in Example 3. After 48 h, the medium was changed and the cells were incubated with CMT-3 for 2 hours before stimulating them with 100 $\mu$g/ml LPS. DMSO was used as a carrier for the modulators and DMSO concentration was maintained (<0.01% v/v) in the cultures. Equivalent amount of DMSO was also added to the control cultures. The expression of COX-2 was examined by Western blot analysis (FIG. 4B) as described above.

EXAMPLE 5

Effect of CMT-8 on Spontaneous Release of Nitric Oxide and PGE$_2$ Produced by OA-Affected Cartilage Human osteoarthritis affected cartilage spontaneously release nitric oxide (NO) and PGE$_2$ in the medium as previously reported (Amin et al, 1995a; 1997a). The OA-organ cultures were set up as described (Amin et al, 1995a; 1997a). Briefly, total knee articular cartilage from tibial plateau and femoral condyle were harvested from OA-affected patients. The cartilage was mixed and cut into 3-mm discs and 4–6 discs were placed in triplicate or quadruplicate, in a 24-well plate in 2.0 ml of Ham's F-12 medium supplemented with 0.2% endotoxin free human albumin, 10 mM Hepes pH 7.4 and antibiotics in the presence of various modulators, as previously described (Amin et al, 1995a; 1997a). CMT-8 was used at pharmacologically relevant concentrations in DMSO (<0.01% final concentration) as carrier. An equivalent amount of DMSO was also added in the control cultures.

Figure 5:
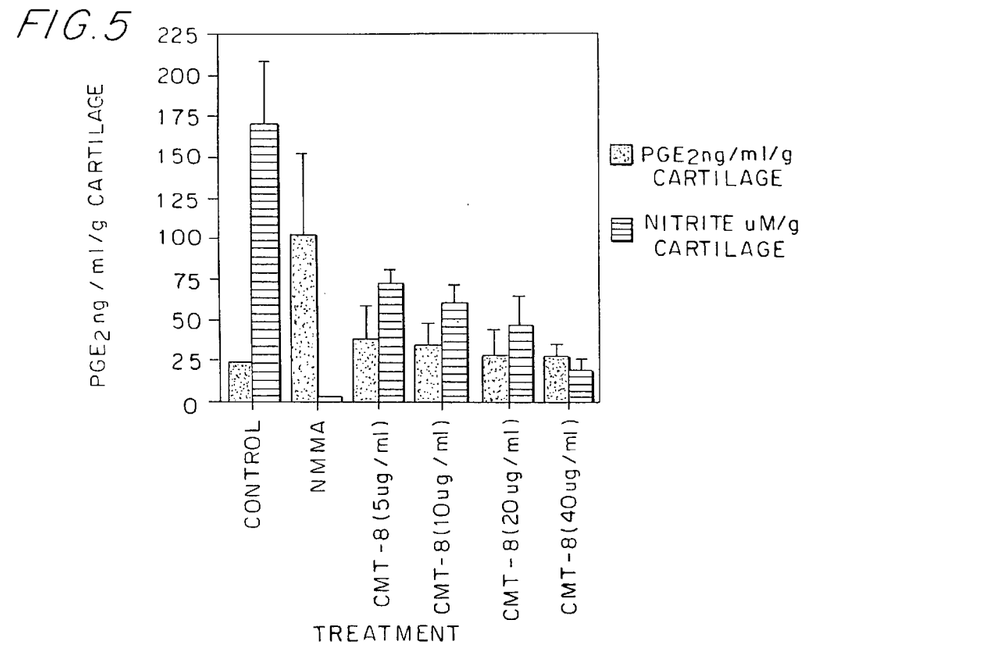
FIG. 5 shows the effect of CMT-8 on spontaneous nitrite and $PGE_2$ production by OA-affected cartilage.

The nitric oxide synthase (NOS) inhibitor L-NMMA inhibits NOS and NO production but augments PGE$_2$ production (Amin et al, 1997a). In contrast, another NOS inhibitor CMT-8 not only inhibits NOS and NO production but also inhibits PGE$_2$ in a dose dependent manner (FIG. 5 and Table 2 below). The p value between control and CMT-8 treated values for PGE$_2 \leq 0.1$ (insignificant) whereas the p values between NMMA treated cartilage and CMT-8 treated cartilage was $\leq 0.001$ (significant). The data are represented as mean±SD as examined by T test when n=3. The results for CMT 1, 2, 3, 5 and 8 are shown in Table 2 below. Data represent±SD value as determined by Student's t test n=4. The P values described are compared with control unstimulated OA-cartilage. The data represents one of the two similar experiments. P values for PGE$_2$ and Nitrite=$^a \leq 0.5$; $^b \leq 0.1$; $^c \leq 0.05$; $^d \leq 0.01$.

TABLE 2

| OA Cartilage | Nitrite (μM) | % Inhibition | PGE$_2$ (ng/ml) | % Inhibition |
|---|---|---|---|---|
| Undiluted | 94.0 ± 25.0 | — | 221.8 ± 70.3 | — |
| +CMT-1 (5 μg/ml) | 82.0 ± 33.0$^a$ | — | 131.8 ± 37.7$^b$ | — |
| +CMT-2 (5 μg/ml) | 84.0 ± 20.0$^a$ | — | 145.2 ± 61.6$^b$ | — |
| +CMT-3 (5 μg/ml) | 75.0 ± 25.0$^b$ | — | 88.0 ± 21.4$^d$ | 60 |
| +CMT-5 (5 μg/ml) | 111.0 ± 8.0$^a$ | — | 162.6 ± 65.3$^a$ | — |
| +CMT-8 (5 μg/ml) | 47.0 ± 22.0$^d$ | 40 | 94.7 ± 39.2$^c$ | 58 |
| +Minocycline (10 μg/ml) | 66.0 ± 17.0$^c$ | 30 | 314.6 ± 58.4$^b$ | — |

The data in Table 2 above demonstrate the ability of CMT-3 and CMT-8 to significantly inhibit the spontaneous generation of NO and PGE$_2$ by OA-affected human cartilage. The data demonstrate the superiority of the CMTs to minocycline, which suppresses NO production, but stimulates PGE$_2$ production.

EXAMPLE 6

Release of TNFα by Permanently Transfected HEK 293 Cells with Human ProTNFα Wild and Mutant ProTNFα

Figure 6:
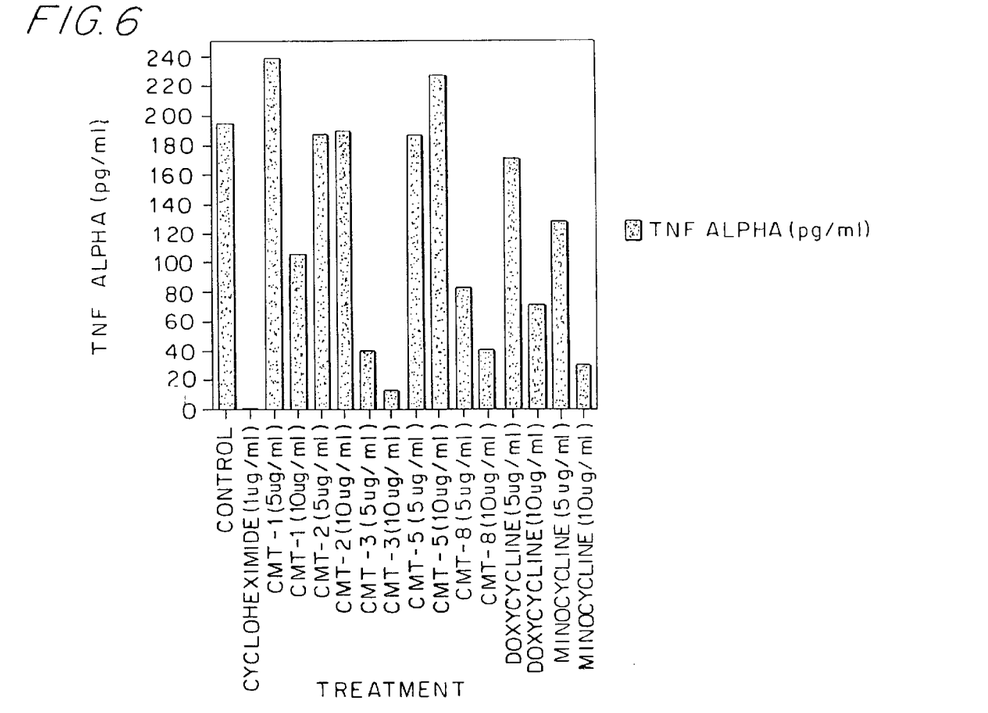
FIG. 6 shows the release of TNFα from permanently transfected HEK 293 cells with human wild-type proTNFα or mutant proTNFα.

Human HEK 293 cells (ATCC 1573-CRL) were grown in minimal essential medium (Gibco-BRL), 10% FCS, 2 mM glutamine, penicillin (50 μM/ml) and streptomycin (50 μg/ml) as described by the American Type Culture Collection (ATCC). HEK 293 cells were transfected with the proTNFα cDNA (wild) to prepare a stable cell line. The HEK cells were transfected using calcium phosphate method as described by the supplier (Gibco BRL, Cat. No. 18306-019). The TNFα convertase cleavage sequence, Ala-Gln-Ala-Val-Arg-Ser (SEQ ID NO:2), was deleted from the parent proTNFα to generate a mutant proTNFα. A mutant form of proTNFα cDNA which could not be cleaved by the endogenous TNFα convertase (TACE) to release soluble TNFα was also transfected in separate human HEK 293 cells. The soluble TNFα was estimated by ELISA from the wild type and mutant transfected cells from the medium (FIG. 6). The control untransfected cells did not release detectable amounts of soluble TNFα in the medium. The wild type membrane bound proTNFα transfected in HEK 293 cells cleaved the proTNFα to the soluble TNFα and released it in the medium. However, the proTNFα mutant, which was expressed in HEK 293 cells could not be recognized by the endogenous TNFα convertase and therefore no detectable amount of TNFα in the medium could be seen. These cell lines are excellent tools to screen for compounds that inhibit endogenous TACE activity by estimating soluble TNFα in the medium.

EXAMPLE 7

Effect of CMT-3 on TNFα release in the medium by HEK 293 cells permanently transfected with Human ProTNFα

Figure 7:
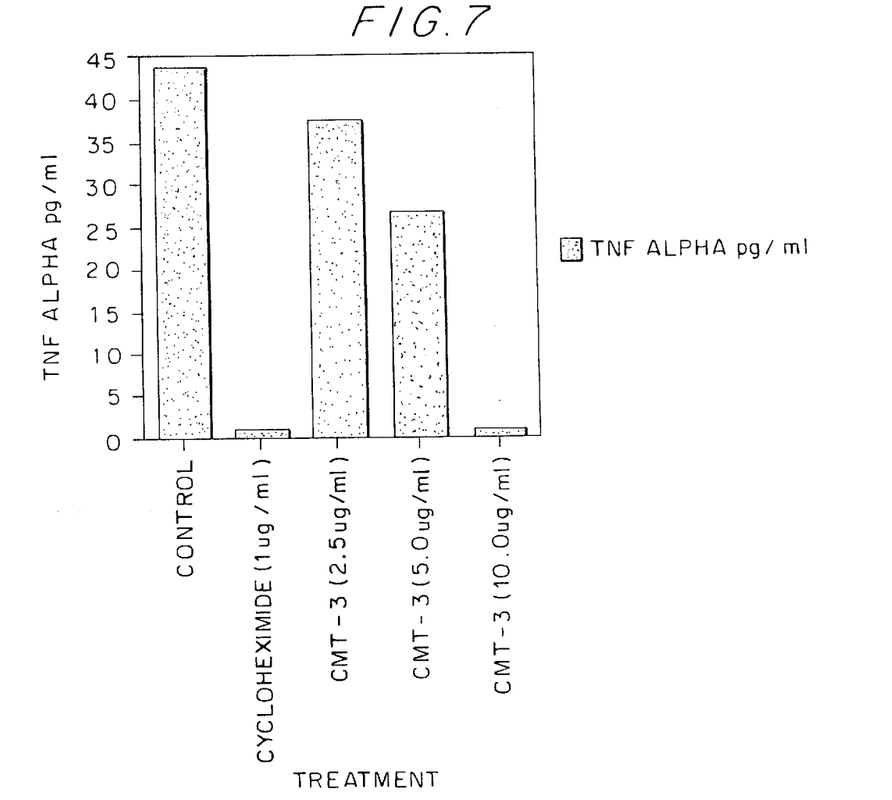
FIG. 7 shows the effect of CMT-3 on TNFα release in the medium by HEK 293 cells permanently transfected with human proTNFα.

HEK 293 cells were grown as previously described by American Type Culture Collection (ATCC). These cells were permanently transfected with proTNFα cDNA and these permanently transfected cells spontaneously released TNFα in the medium which was estimated by ELISA. The HEK 293 cells were incubated with CMT-3 to examine the effects of CMT-3 on TNFα release in the medium. FIG. 7 shows that CMT-3 inhibits TNFα release in the medium in a dose dependent manner. Cycloheximide as expected also inhibited the release of TNFα in the medium.

EXAMPLE 8

Effects of CMTs/Tetracycline on the Release of TNFα

Figure 8:
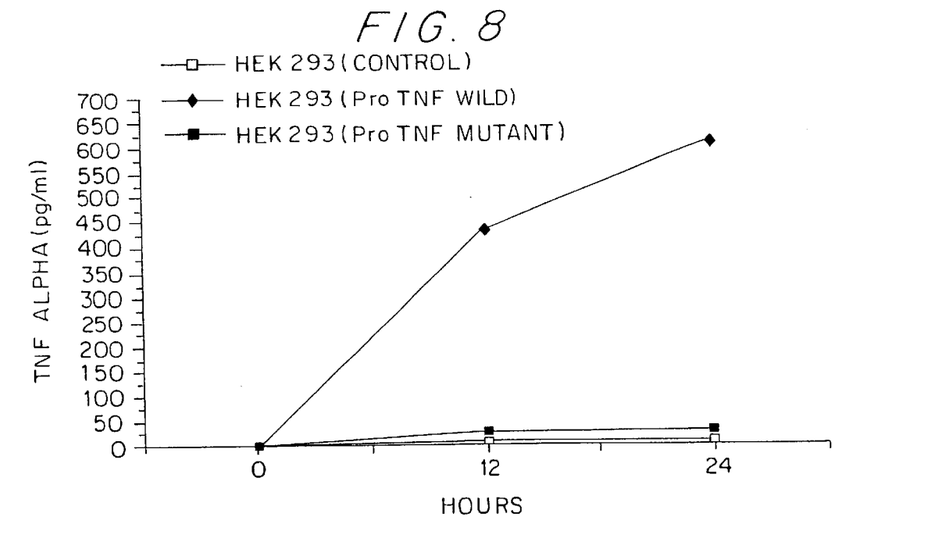
FIG. 8 shows the effect of tetracyclines on the release of TNFα in the medium from human HEK 293 permanently transfected with human proTNFα.

HEK 293 cells were grown under the conditions previously described by ATCC. Various compounds, including CMT-3 and doxycycline/minocyclines were incubated with proTNFα transfected HEK 293 cells releasing TNFα in the medium at 16 hours. The spontaneous release of TNFα by permanently transfected proTNFα$^+$ HEK 293 is shown in FIG. 6 as a control in this experiment. Soluble TNFα was estimated by ELISA from the medium. As expected, cycloheximide was shown to inhibit the release of TNFα (FIG. 8). In FIG. 8, CMT-3, CMT-8 and CMT-1, but not CMT-2 and CMT-5, inhibit the spontaneous TNFα release. Similarly, doxycycline and minocycline also inhibit TNFα release. This experiment shows that a selected number of CMTs have the property to inhibit TNFα release or the activity of TNFα convertase enzyme (TACE).

EXAMPLE 9

Effect of CMTs on COX-2 Specific Activity In Vitro

Raw 264.7 cells were stimulated with LPS and cell-free extracts were prepared as follows. RAW 264.7 cells were induced with LPS (100 ng/ml) in the presence or absence of tetracyclines or hydrocortisone for 14–20 hours. Following induction, the cells were pelleted at 4° C. and resuspended in Tris buffer: 10 mM, pH 7.4 containing 10 μg/ml each of chymostatin, antipain, leupeptin and pepstatin, 1 mM DDT and 1 mM PMSF. Cells were lysed in a Polytron PA 1200 homogenizer (Kinematica AG, Switzerland) with the cocktail of protease inhibitors after 3 cycles of rapid freeze-thawing. The lysate was centrifuged at 18,000 at 4° C. in an eppendorf centrifuge, and the resulting supernatant was used as cell-free extracts. The protein was measured by BCA assay reagent (Pierce, Rockford, Ill.) using BSA as standard. The cell-free enzyme assay was performed as previously described by Vane et al (1994) using total unfractionated cell extracts, and the amount of PGE$_2$ was estimated by RIA. The specific enzyme activity was defined as ng of PGE$_2$ released/mg protein/37° C. for 20 minutes.

Addition of 10 μg/ml of CMT-3 (27 μM) and CMT-8 (27 μM), like aspirin (56 μM) and indomethacin (28 μM), to the cell-free extracts significantly inhibited the specific activity of COX-2, whereas the inactive analog of CMTs (CMT-5) had no significant effect (Table 3). These experiments suggest that CMT-3 and CMT-8 interfere with the enzyme activity of COX-2 in cell-free extracts, and their ability to inhibit COX-2 mediated PGE$_2$ production in vitro was similar to aspirin and indomethacin. These experiments also show a novel mechanism of action of CMTs on COX-2 and separates them from the generic tetracyclines. The possibility of these CMTs binding to COX-2 (like aspirin) cannot be ruled out. Although there is a significant increase in the accumulation of the COX-2 protein on the whole, these experiments may also explain the net decrease in the PGE$_2$ accumulation in CMT treated cells.

TABLE 3

Effect of CMTs on COX-2 Specific Activity In Vitro

| Treatment | COX-2 Specific Activity (PGE$_2$ ng/mg protein) | P ≦ | % Inhibition |
|---|---|---|---|
| Control + Substrate | 8.6 ± 0.3 | | |
| CMT-3 (10 μg) | 2.8 ± 4.0 | 0.005 | 70 |
| CMT-5 (10 μg) | 9.8 ± 0.4 | 0.02 | — |
| CMT-8 (10 μg) | 4.3 ± 0.1 | 0.001 | 54 |
| Aspirin (μg) | 2.1 ± 0.1 | 0.004 | 77 |
| Indomethacin (10 μg) | 2.6 ± 0.1 | 0.005 | 72 |

RAW 264.7 cells were stimulated with 1 μg/ml of LPS for 16 hours and cell-free extracts were prepared as described above. The extracts were incubated with different modulators for 20 minutes at 37° C. before adding the substrate to initiate the enzyme reaction, which was terminated after 30 minutes by heat inactivation. The data represent one of the two experiments, the PGE$_2$ analysis from each sample was done in triplicates n=3. The p value is a comparison between control and experimentals.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Amin et al, *J. EXP. Med.* 182:2097–2102 (1995a)
Amin et al, *Proc. Natl. Acad. Sci. USA* 93:14014–14019 (1995b)
Amin et al, *J. Clin. Inv.* 99:1231–1237 (1997a)
Amin et al, *FEBS* 410:259–264 (1997b)
Aydelotte et al, *Conn. Tissue* 18:205 (in press for 1998)
Brinckerhoff, C. E., *Arthritis Rheum.* 34:1073–1075 (1991)
DeClerck et al, *Annals N.Y. Acad Sci.* 732:222–232 (1994)
Golub et al, *Crit. Rev. Oral Biol. Med.* 2:297–322 (1991)
Golub et al, *Curr. Opin. Dent.* 2:80–90 (1992)
Greenwald, R. A., *Annals N.Y. Acad. Sci.* 732:181–198 (1994)
Maragoudakis et al, *Annals N.Y. Acad. Sci.* 732:280–293 (1994)
Mohtai et al, *J. Clin. Inv.* 92:179–185 (1993)
Ramamurthy et al, *Annals N.Y. Acad. Sci.* 732:427–430 (1994)
Rifkin et al, *Annals N.Y. Acad. Sci.* 732:165–180 (1994)
Salvemini et al, *Proc. Natl. Acad. Sci. USA* 90:7240–7244 (1993)
Tilley et al, *Ann. Intern. Med.* 122:81–89 (1995)
Uitto et al, *Annals N.Y. Acad. Sci.* 732:140–151 (1994)
Vane et al, *Proc. Natl. Acad. Sci. USA* 91:2046–2050 (1994)
Yu et al, *Arthritis Rheum.* 35:1150–1159 (1992)

What is claimed is:

1. A method for treating a disease or disorder associated with an elevated level of TNFα and/or products of COX-2 activity, comprising administering to a subject in need thereof a chemically modified tetracycline compound having negligible anti-microbial activity in an amount sufficient to reduce the expression or activity of COX-2 and/or TNFα in the subject to treat a disease or disorder associated with an elevated level of TNFα and/or products of COX-2 activity selected from the group consisting of multiple sclerosis, septic shock, graft-vs.-host disease, cerebral malaria, cachexia associated with HIV infection, brain ischemia, inflammatory bowel disease, and neurodegenerative disorders.

2. The method of claim 1, wherein the chemically modified tetracycline compound having negligible anti-microbial activity is selected from the group consisting of CMT-1, CMT-3, and CMT-8.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Unknown
<220> FEATURE:
<223> OTHER INFORMATION: Unknown
<221> NAME/KEY: PEPTIDE
<222> LOCATION: (1)..(4)

<400> SEQUENCE: 1

Gln Ala Val Arg
1
```

```
-continued

<210> SEQ ID NO 2
<211> LENGTH: 6
<212> TYPE: PRT
<213> ORGANISM: Unknown
<220> FEATURE:
<223> OTHER INFORMATION: Unknown
<221> NAME/KEY: PEPTIDE
<222> LOCATION: (1)..(6)

<400> SEQUENCE: 2

Ala Gln Ala Val Arg Ser
1               5
```